United States Patent [19]

Bundy

[11] 4,268,669

[45] May 19, 1981

[54] 9-DEOXY-9-METHYLENE-5,6-DIDEHYDRO-PGF$_1$ AMIDES

[75] Inventor: Gordon L. Bundy, Portage, Mich.

[73] Assignee: The Upjohn Company, Kalamazoo, Mich.

[21] Appl. No.: 116,076

[22] Filed: Jan. 28, 1980

Related U.S. Application Data

[62] Division of Ser. No. 35,144, May 1, 1979.

[51] Int. Cl.$^3$ ............................................. C07C 177/00
[52] U.S. Cl. .................................. 542/429; 260/404; 260/464; 560/29; 560/45; 562/453; 562/452; 562/455; 564/80; 564/87; 564/89; 564/90; 564/95; 564/98; 564/152; 564/189; 564/158

[58] Field of Search ............................ 560/121, 29, 45; 260/559, 404, 464, 556 AC, 557 R, 558 R, 561 R; 542/429; 562/453

[56] References Cited

U.S. PATENT DOCUMENTS 4,123,441 10/1978 Johnson ............................ 260/345.2

Primary Examiner—Robert Gerstl
Attorney, Agent, or Firm—Robert A. Armitage

[57] ABSTRACT

The present invention particularly relates to novel 9-deoxy-9-methylene-5,6-didehydro-PGF$_1$ amides and methods for their preparation in pharmacological use.

1 Claim, No Drawings

9-DEOXY-9-METHYLENE-5,6-DIDEHYDRO-PGF$_1$ AMIDES

CROSS REFERENCE TO RELATED APPLICATIONS

The present application is a divisional application of U.S. Ser. No. 035,144, filed May 1, 1979, now pending.

BACKGROUND OF THE INVENTION

The present invention particularly relates to novel 9-deoxy-9-methylene-5,6-didehydro-PGF$_1$ amides and methods for their preparation and pharmalogical use.

The essential material constituting the disclosure of the preparation and pharmacological use of the compounds of the present invention is incorporated here by reference from U.S. Ser. No. 035,144 and U.S. Pat. No. 4,060,534. The latter patent describes certain 9-deoxy-9-methylene-PGF-type compounds which are cis isomers of the novel compounds disclosed herein.

PRIOR ART

Known in the art are trans-5,6-didehydro PG$_1$ compounds and 9-deoxy-9-methylene PGF compounds. Trans-5,6-didehydro prostaglandins are described in U.S. Pat. Nos. 3,759,978, 3,823,180, 3,832,379, and 3,821,291.

SUMMARY OF THE INVENTION

The present invention particularly provides: a prostaglandin analog of formula VI

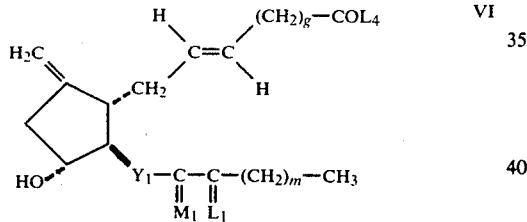

wherein Y$_1$ is trans—CH=CH—, —C≡C—, —CH$_2$CH$_2$—, or cis—CH=CH—;
wherein M$_1$ is $\alpha$-R$_5$:$\beta$-OH or $\alpha$-OH:$\beta$-R$_5$, wherein R$_5$ is hydrogen or methyl;
wherein L$_1$ is $\alpha$-R$_3$:$\beta$-R$_4$, $\alpha$-R$_4$:$\beta$-R$_3$, or a mixture of $\alpha$-R$_3$:$\beta$-R$_4$ and $\alpha$-R$_4$:$\beta$-R$_3$ wherein R$_3$ and R$_4$ are hydrogen, methyl, or fluoro, being the same or different, with the proviso that one of R$_3$ and R$_4$ is fluoro only when the other is hydrogen or fluoro;
wherein g is 3, 4, or 5;
wherein m is one to 5, inclusive; and
wherein L$_4$ is (a) amino of the formula —NR$_{21}$R$_{22}$, wherein R$_{21}$ and R$_{22}$ are
 (i) hydrogen;
 (ii) alkyl or one to 12 carbon atoms, inclusive;
 (iii) cycloalkyl of 3 to 10 carbon atoms, inclusive;
 (iv) aralkyl of 7 to 12 carbon atoms, inclusive;
 (v) phenyl;
 (vi) phenyl substituted with one, 2 or 3 chloro, alkyl of one to 3 carbon atoms, inclusive, hydroxy, carboxy, alkoxycarbonyl of one to 4 carbon atoms, inclusive, or nitro;
 (vii) carboxyalkyl of 2 to 5 carbon atoms, inclusive;
 (viii) carbamoylalkyl of 2 to 5 carbon atoms, inclusive;
 (ix) cyanoalkyl of 2 to 5 carbon atoms, inclusive;
 (x) acetylalkyl of 3 to 6 carbon atoms, inclusive;
 (xi) benzoylalkyl of 7 to 11 carbon atoms, inclusive;
 (xii) benzoylalkyl substituted by one, 2 or 3 carbon atoms, inclusive, hydroxy, alkoxy of one to 3 carbon atoms, inclusive, carboxy, alkoxycarbonyl of one to 4 carbon atoms, inclusive, or nitro;
 (xiii) pyridyl;
 (xiv) pyridyl substituted by one, 2 or 3 chloro, alkyl of one to 3 carbon atoms, inclusive, or alkoxy of one to 3 carbon atoms, inclusive;
 (xv) pyridylalkyl of 6 to 9 carbon atoms, inclusive;
 (xvi) pyridylalkyl substituted by one, 2 or 3 carbon atoms, inclusive, hydroxy or alkoxy of one to 3 carbon atoms, inclusive;
 (xvii) hydroxyalkyl of one to 4 carbon atoms, inclusive;
 (xviii) dihydroxyalkyl of one to 4 carbon atoms; or
 (xix) trihydroxyalkyl of one to 4 carbon atoms; with the further proviso that not more than one of R$_{21}$ and R$_{22}$ is other than hydrogen or alkyl;

(b) cycloamino selected from the group consisting of
 (i) pyrrolidino,
 (ii) piperidino,
 (iii) morpholino,
 (iv) piperazino,
 (v) hexamethyleneimino,
 (vi) pyrrolino,
 (vii) 3,4-didehydropiperidinyl, or
 (viii) pyrrolidino, piperidino, morpholino, piperazino, hexamethyleneimino, pyrrolino, or 3,4-didehydropiperidinyl substituted by one or two alkyl of one to 12 carbon atoms, inclusive;

(c) carbonylamino of the formula —NR$_{23}$COR$_{21}$, wherein R$_{23}$ is hydrogen or alkyl of one to 4 carbon atoms and R$_{21}$ is other than hydrogen, but otherwise as defined above; or (d) sulfonylamino of the formula —NR$_{23}$SO$_2$R$_{21}$, wherein R$_{21}$ and R$_{23}$ are as defined in (c).

I claim:
1. A prostaglandin analog of formula VI

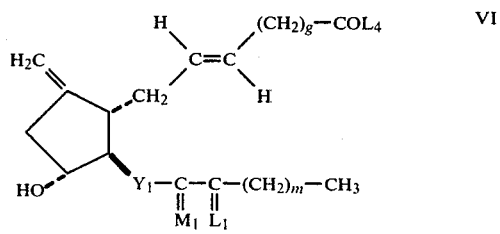

wherein Y$_1$ is trans—CH=CH—, —C≡C—, —CH$_2$CH$_2$—, or cis—CH=CH—;
wherein M$_1$ is $\alpha$-R$_5$:$\beta$-OH or $\alpha$-OH:$\beta$-R$_5$, wherein R$_5$ is hydrogen or methyl;
wherein L$_1$ is $\alpha$-R$_3$:$\beta$-R$_4$, $\alpha$-R$_4$:$\beta$-R$_3$, or a mixture of $\alpha$-R$_3$:$\beta$-R$_4$ and $\alpha$-R$_4$:$\beta$-R$_3$ wherein R$_3$ and R$_4$ are hydrogen, methyl, or fluoro, being the same or different, with the proviso that one of $R_3$ and $R_4$ is fluoro only when the other is hydrogen or fluoro;
wherein g is 3, 4, or 5;
wherein m is one to 5, inclusive, and
wherein $L_4$ is
  (a) amino of the formula —$NR_{21}R_{22}$, wherein $R_{21}$ and $R_{22}$ are
    (i) hydrogen;
    (ii) alkyl or one to 12 carbon atoms, inclusive;
    (iii) cycloalkyl of 3 to 10 carbon atoms, inclusive;
    (iv) aralkyl of 7 to 12 carbon atoms, inclusive;
    (v) phenyl;
    (vi) phenyl substituted with one, 2 or 3 chloro, alkyl of one to 3 carbon atoms, inclusive, hydroxy, carboxy, alkoxycarbonyl of one to 4 carbon atoms, inclusive, or nitro;
    (vii) carboxyalkyl of 2 to 5 carbon atoms, inclusive;
    (viii) carbamoylalkyl of 2 to 5 carbon atoms, inclusive;
    (ix) cyanoalkyl of 2 to 5 carbon atoms, inclusive;
    (x) acetylalkyl of 3 to 6 carbon atoms, inclusive;
    (xi) benzoylalkyl of 7 to 11 carbon atoms, inclusive;
    (xii) benzoylalkyl substituted by one, 2 or 3 carbon atoms, inclusive, hydroxy, alkoxy of one to 3 carbon atoms, inclusive, carboxy, alkoxycarbonyl of one to 4 carbon atoms, inclusive, or nitro;
    (xiii) pyridyl;
    (xiv) pyridyl substituted by one, 2 or 3 chloro, alkyl of one to 3 carbon atoms, inclusive, or alkoxy of one to 3 carbon atoms, inclusive;
    (xv) pyridylalkyl of 6 to 9 carbon atoms, inclusive;
    (xvi) pyridylalkyl substituted by one, 2 or 3 carbon atoms, inclusive, hydroxy or alkoxy of one to 3 carbon atoms, inclusive;
    (xvii) hydroxyalkyl of one to 4 carbon atoms, inclusive;
    (xviii) dihydroxyalkyl of one to 4 carbon atoms; or
    (xix) trihydroxyalkyl of one to 4 carbon atoms;
    with the further proviso that not more than one of $R_{21}$ and $R_{22}$ is other than hydrogen or alkyl;
  (b) cycloamino selected from the group consisting of
    (i) pyrrolidino,
    (ii) piperidino,
    (iii) morpholino,
    (iv) piperazino,
    (v) hexamethyleneimino,
    (vi) pyrrolino,
    (vii) 3,4-didehydropiperidinyl, or
    (viii) pyrrolidino, piperidino, morpholino, piperazino, hexamethyleneimino, pyrrolino, or 3,4-didehydropiperidinyl substituted by one or two alkyl of one to 12 carbon atoms, inclusive;
  (c) carbonylamino of the formula—$NR_{23}COR_{21}$, wherein $R_{23}$ is hydrogen or alkyl of one to 4 carbon atoms and $R_{21}$ is other than hydrogen, but otherwise as defined above; or
  (d) sulfonylamino of the formula —$NR_{23}SO_2R_{21}$, wherein $R_{21}$ and $R_{23}$ are as defined in (c).

* * * * *